United States Patent [19]
Martinez-Lara

[11] Patent Number: 5,689,224
[45] Date of Patent: Nov. 18, 1997

[54] REACTOR TO MODIFY ENVIRONMENT AND CREATE ELECTRO-MAGNETIC FIELDS

[76] Inventor: Estanislao Martinez-Lara, Trinidad #322 Col. Vista Hermosa 64620, Monterrey, Nuevo Leon, Mexico

[21] Appl. No.: 572,011

[22] Filed: Dec. 14, 1995

[51] Int. Cl.[6] .................... H01F 1/00; B01J 19/08; A61N 1/00
[52] U.S. Cl. .................. 335/219; 422/186.01; 600/13; 600/14
[58] Field of Search .................. 600/9, 15; 96/1, 96/2; 335/219, 296–306; 422/186.01–186.03

[56] References Cited

U.S. PATENT DOCUMENTS

| | | | |
|---|---|---|---|
| 2,036,899 | 4/1936 | Wait | 422/186.01 |
| 2,055,809 | 9/1936 | Wait | 422/186.01 |

Primary Examiner—Lincoln Donovan
Assistant Examiner—Raymond Barrera
Attorney, Agent, or Firm—Laurence R. Brown

[57] ABSTRACT

An apparatus and its mechanism, and more specifically to a reactor that comprehends in combination, one or several continuous walls made with glass and non ferrous metallic separating plates, which converge in its upper part, which are partially placed inside a box, in which interior additionally are placed a transformer, a reflecting mirror, and a fan by means of which air is forced through the walls; the invention also combines a plurality of accessories, including a long cushion, seat cushions and car seats interconnected to the reactor's body and over which any one may rest to benefit his or her cells, molecules and genes for the operation of the reactor. It also includes one or several rotating pointers, sliding transmitters and a platform with spheres, interconnected to the pyramid by means of plugs, making it possible to massage one person's skin.

7 Claims, 13 Drawing Sheets

REACTOR TO MODIFY ENVIRONMENT AND CREATE ELECTRO-MAGNETIC FIELDS

BACKGROUND OF THE INVENTION

From immemorial time, man kind is searching for resources provided by nature, to improve its own life and its environment; through time many have been the mechanisms, and in some way human inventions, for health care and better living.

The present invention, for the first time provides a simple and practical reactor capable of improving conditions in the environment and modifying favorably the physical status of the human body, in a totally transportable device, easy to place, not only in different locations outdoors, but also inside buildings, houses, commercial places, cars, Etc.

DESCRIPTION OF THE INVENTION

Referring to said figures, this reactor comprises in combination, a box (1), which may adopt any geometric form, it is constructed with dielectric material and it may have legs (2), to provide the possibility of being separated from the floor; a main body (3) and a central body (4B) fit in the box (1), each built with one or several watts, which are built with glass plates (4) and metallic separating plates of non ferrous alloy (5) shorter than the glass plates (4), alternated in such a way that a glass plate is placed (4) followed by a metallic plate of non ferrous alloy (5), in this sequence, as metallic plates are of a non ferrous alloy (5) and smaller than the glass plates (4), spaces (5) are formed between said plates, and air flows through the spaces; bodies (3 and 4B) converge in their upper vertex, forming an equilateral pyramid, a cone, a vault or any other possible form.

For the purpose of holding firmer the plates (4, 5) in position, they rest in a support (6) provided by multiple channels and manufactured from a dielectric material, in which, bases (4A) of the glass plates (4) penetrate, while the metallic plates of non ferrous metallic alloy (5) are captured in a sandwich type position, centered between the glass plates (4). The support (6) is firmly mounted in the internal face (1A) of the wall or walls that build the box (1) and its position is peripheral around the internal face (1A) of the box wall or walls (1).

In the central part of the interior of the box (1) a reflecting mirror is horizontally placed (7), and it rests over a base (8) in an entirely firm position, the center (7A) of the reflecting mirror (7) remains exactly in the center resulting of the convergence (27) of the apex of the wall or walls (3) in such positions, corresponding portions of the glass plates (4) and the metallic plates of a non ferrous alloy (5) are reflected in the mirror (7) in symmetrically equal planes.

Exactly under the mirror (7) and the base (8) an alternating current transformer (9) is located, which may be variable or not, and it is fastened in the box interior and it receives a determined voltage that may be increased. When such increase is produced, the electromagnetic field (9A) is extended in the surroundings of the variable transformer (9), inside the box atmosphere.

Placed exactly under the transformer (9) and properly held to the chassis (10), there is a fan (11) by means of which it is possible to impel air inside the box (1) upwards, such air will circulate forming a luminous turbulence (11A) in the electromagnetic field (9A) created by the transformer and subsequently through the spaces between the glass plates (4). Under these circumstances air is sterilized, oxygenated and deodorized in such a way that when it exits the apparatus it will favorably modify the environment.

The chassis (10) is firmly mounted in the box (1) interior, by means of stringers (12) to which it is joined by fastening means (14) like screw, rivets or the like. Also in the interior of the box (1) is the electric circuit that includes the transformer's (9) correction leads (15), interconnected to the electric circuit of the apparatus.

The transformer (9) operates in combination with the connection leads (15), in order to change the entering voltage into a higher voltage.

The electric circuit located in the box interior, additionally contains a variable selector mechanism (21) by means of which it is possible to increase or decrease the power or voltage that the transformer (9) receives and gives, that is, it can go from 0 (zero) volts to hundred percent of the voltage available from outside. In the circuit itself there are switches (22) by means of which the electric circuit is switched on and off, fuses (23) that protect the circuit of current excessive increases and a pilot (24) to monitor if the apparatus is on or off.

In the external part of the box (1) the switchboard (25) is visible, as well as the different controls (19) which make the operation of the circuit possible and the sockets (30). The reactor containers a plurality of internal cables (29) by means of which the electricity is conducted towards the sockets (30). Cables 29a start at the base (5C) of the metallic plates of non ferrous alloy (5) and they end joined to the sockets (30).

Some peripheral fittings are also part of the invention, among them is a long cushion (28), which is interconnected to the sockets (30) by the connecting cables (28A).

In the same way, parts of the invention are one or several rotating pointers (31), in which bodies are two sections: a handle (31A) and a head (31B), this way the rotating pointer can be managed in such a manner that the head (31B) slides over those areas which in certain moment a person wants to activate and give energy to stimulate said area. The same rotating pointer together with a cable (31C) and connector (31D) will permit the rotating pointer to be plugged to the connecting plate (29). Also part of the invention is a sliding transmitter (36) which together with a cable (36A) and a connector (36B) is connected to the connecting plate (29). Said sliding transmitter (36) may be used over the skin surface that is to be massaged.

In the same way, part of the invention is a platform (34), with spheres (34A) interconnected among themselves and connected to the sockets (30) of the reactor (1) by means of connecting cables (34B). Said platform allows the person wanting to stimulate its cells to stand over it.

Figure 1:
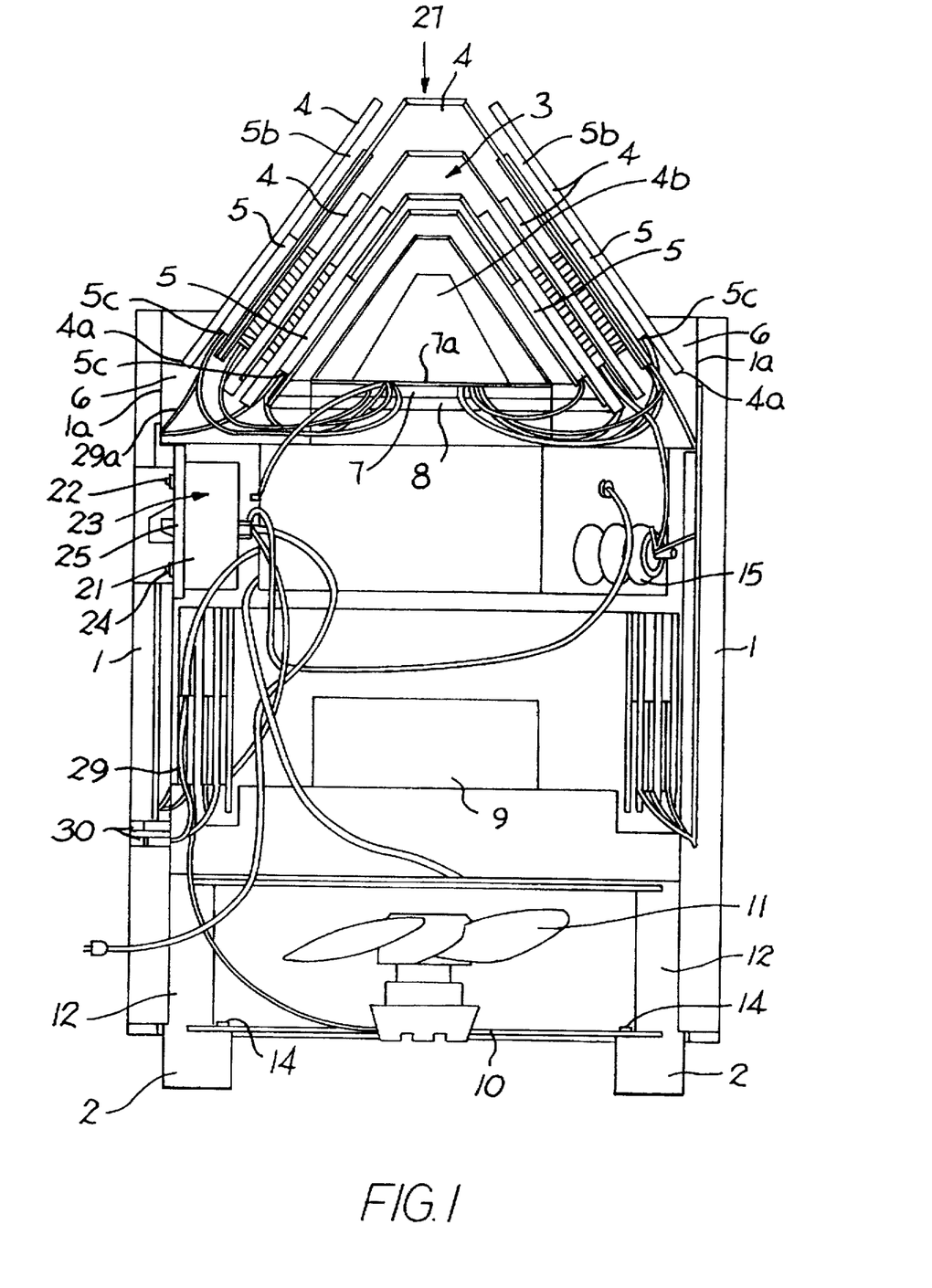
FIG. 1 shows an elevated sectional view of the reactor.
Figure 2:
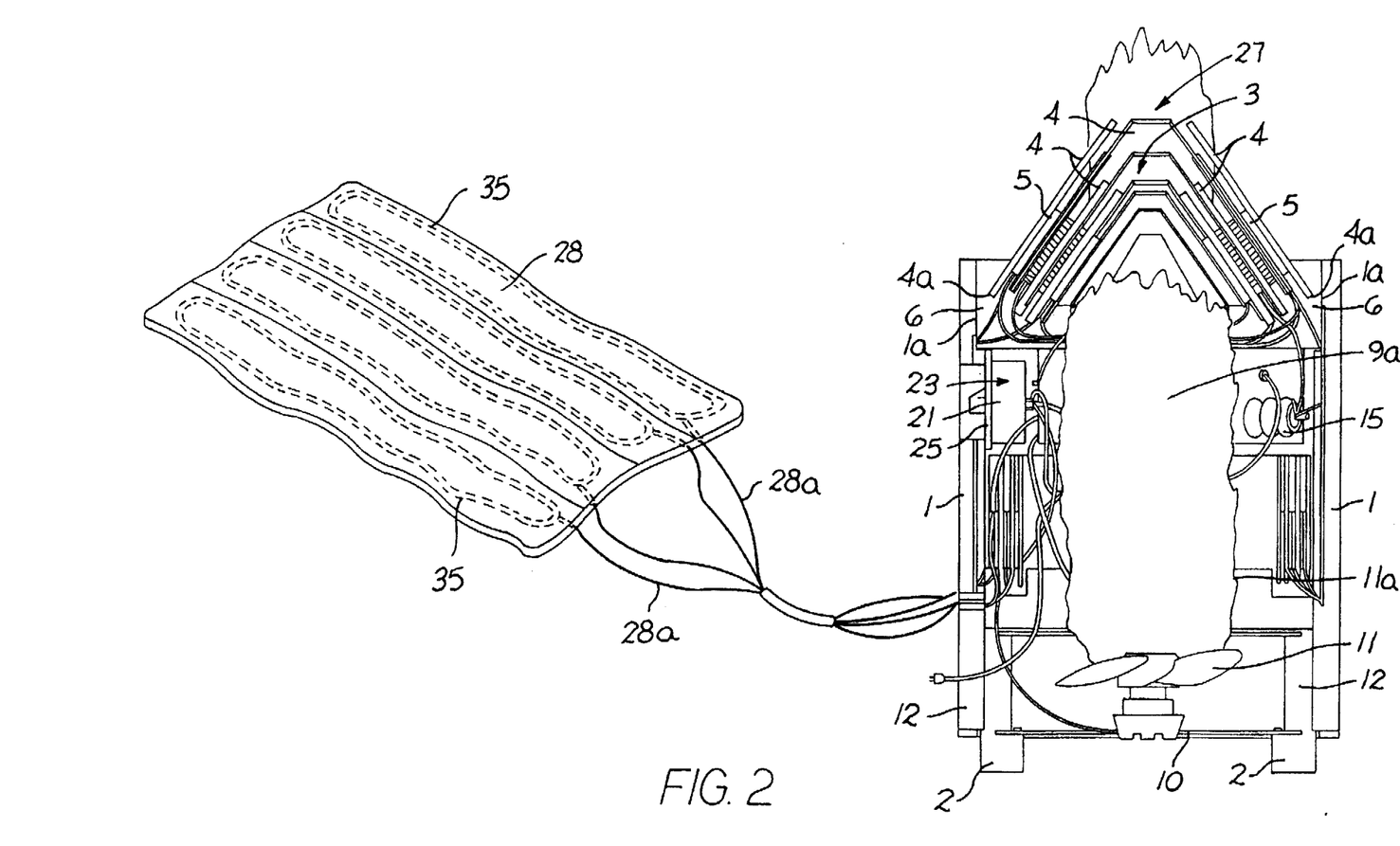
FIG. 2 is a sectional view of the reactor and one long cushion connected to it, in which the turbulence produced and the electromagnetic field created is observed.
Figure 3:
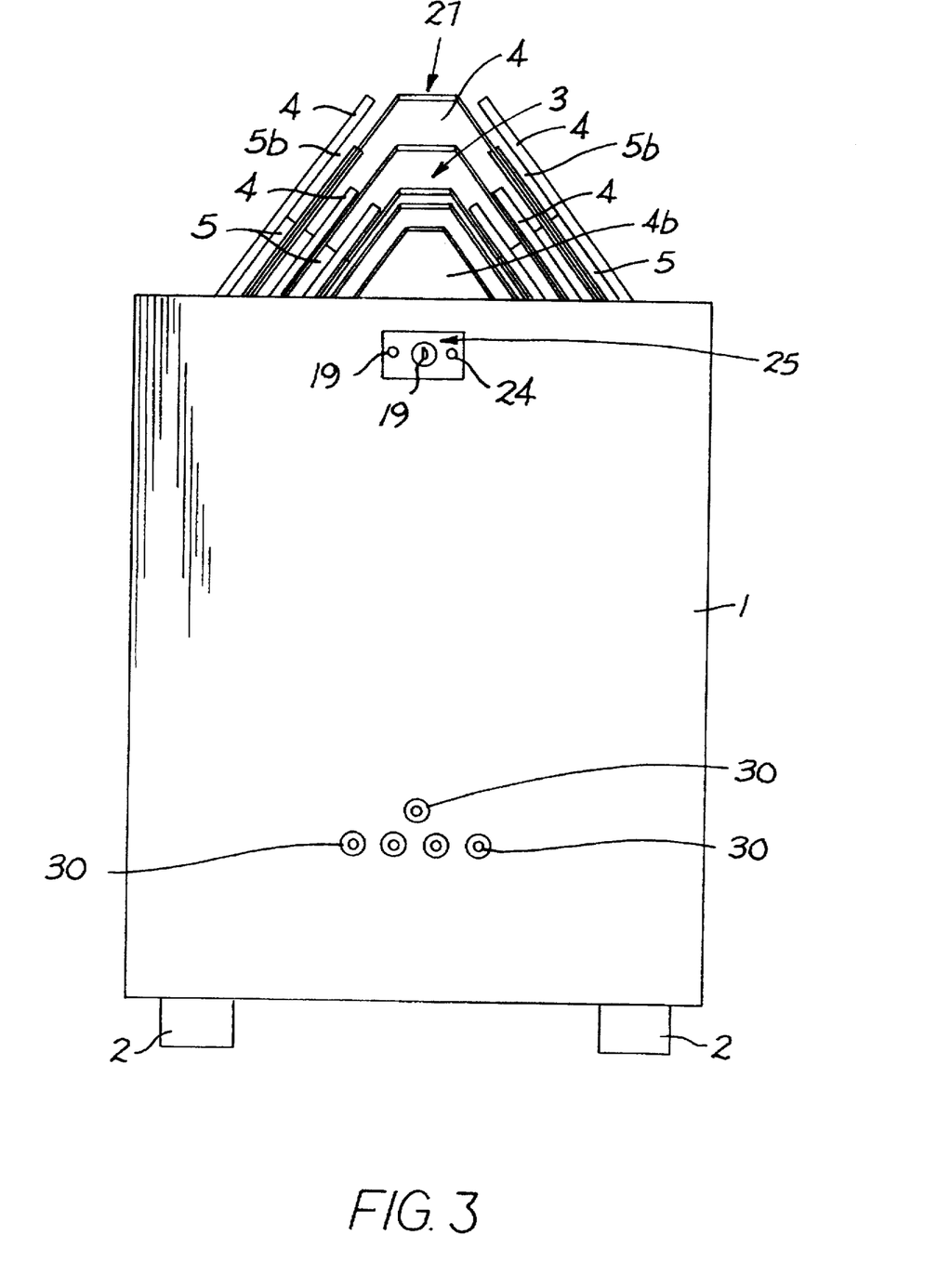
FIG. 3 shows an elevated view of the reactor.
Figure 4:
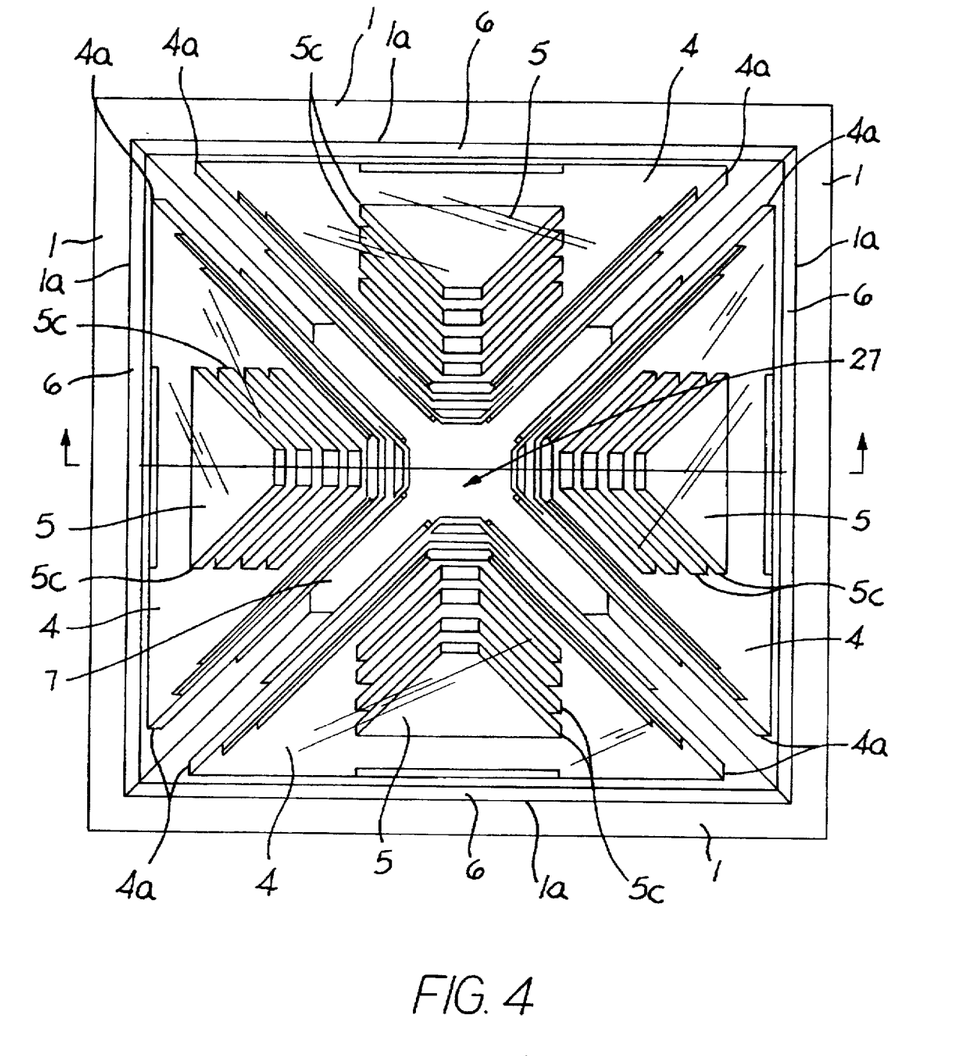
FIG. 4 shows an upper view of the reactor.
Figure 5:
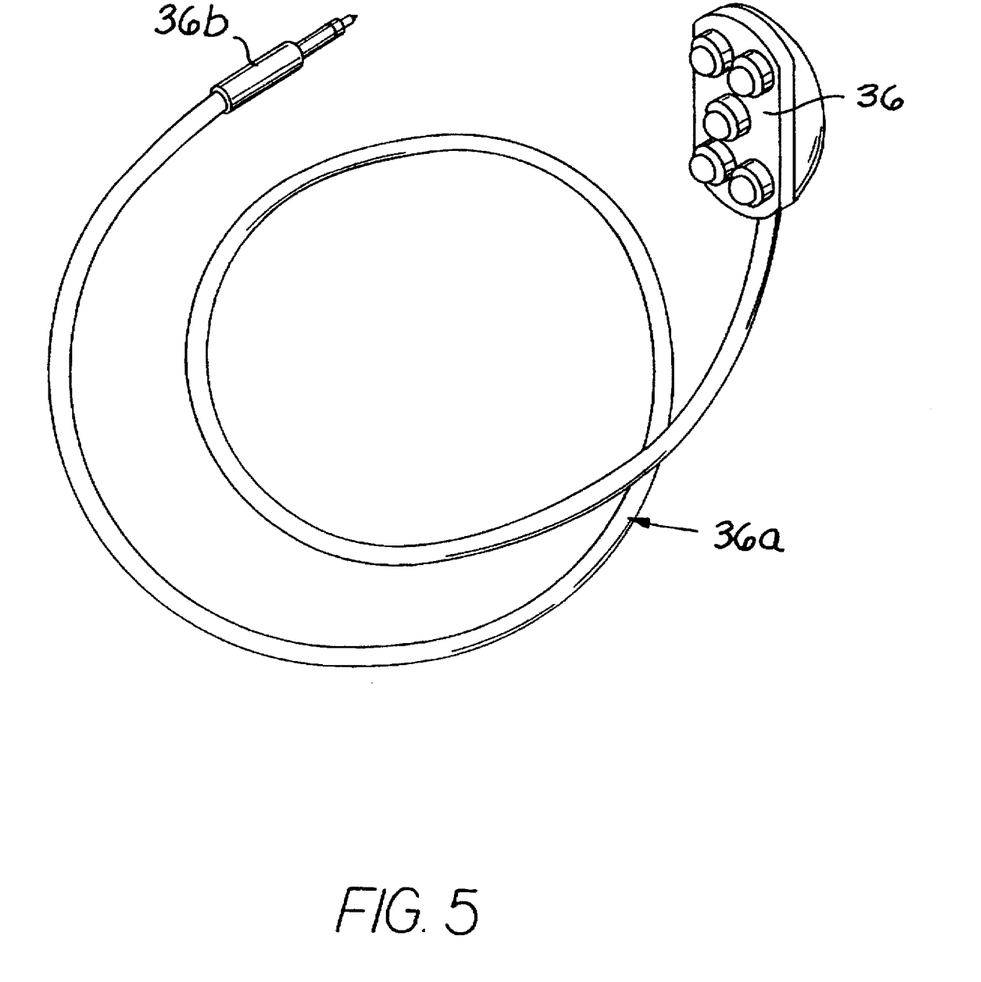
FIG. 5 shows an isometrical view of the sliding transmitter.
Figure 6:
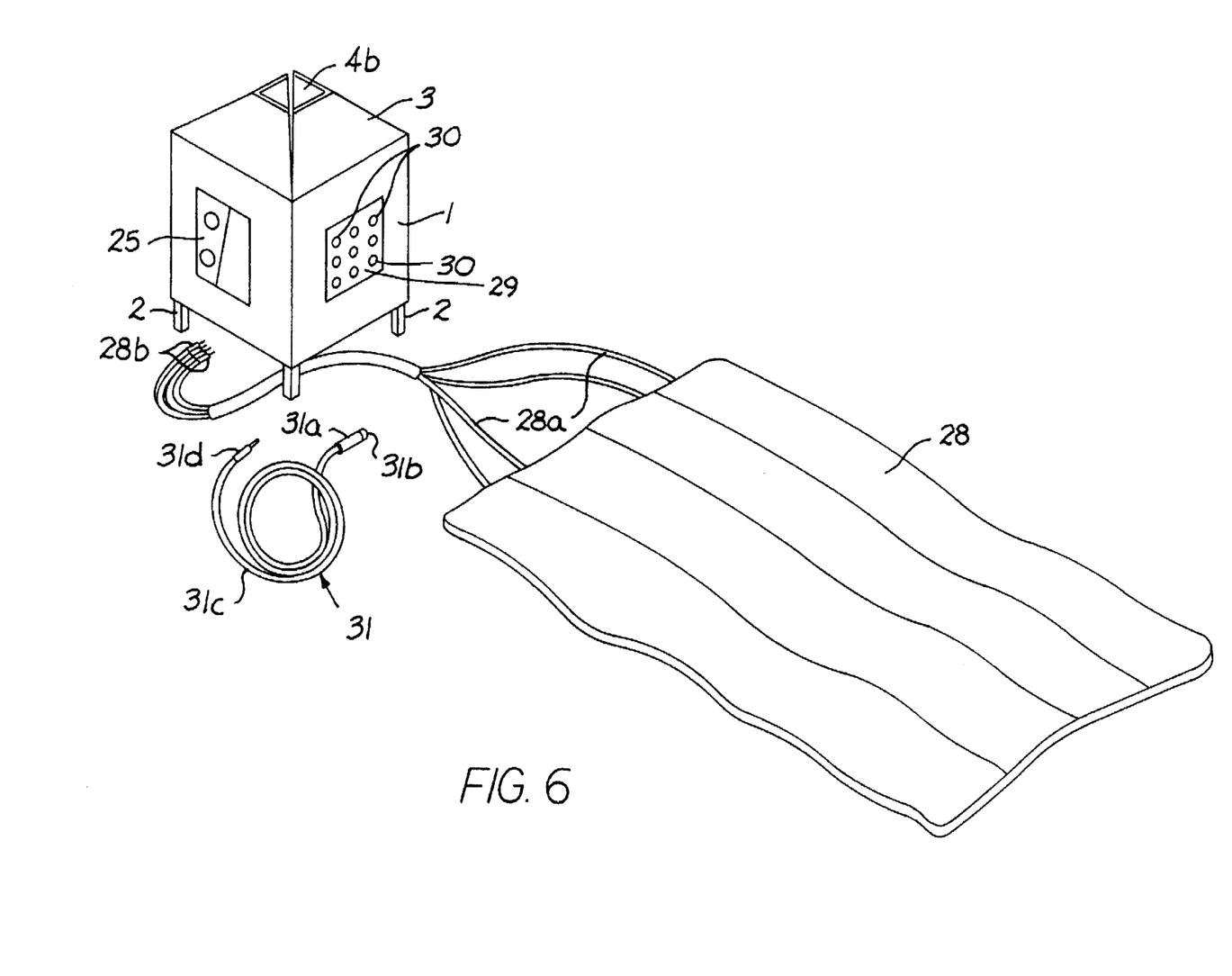
FIG. 6 shows a conventional perspective of the reactor, a long cushion and a rotating pointer, unplugged.
Figure 7:
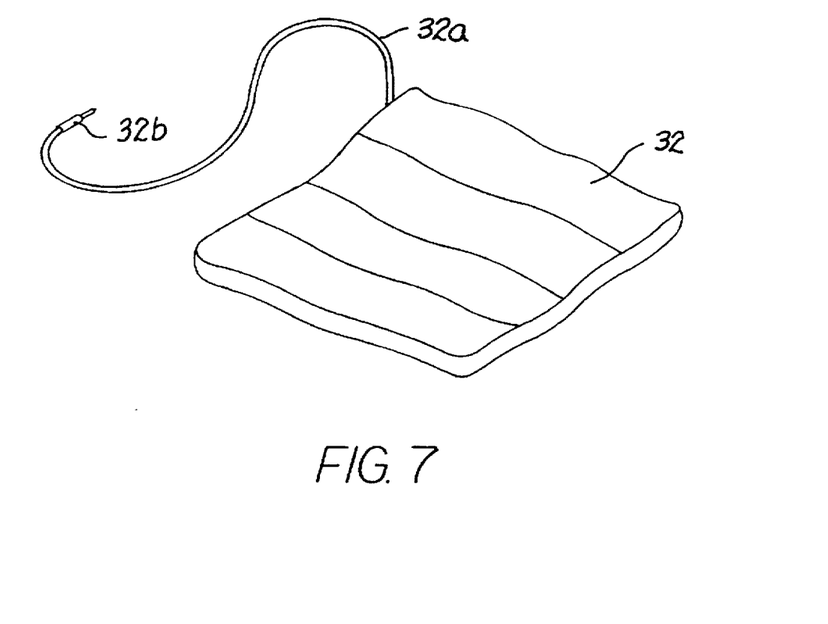
FIG. 7 shows a conventional perspective of a cushion and its connecting cables.
Figure 8:
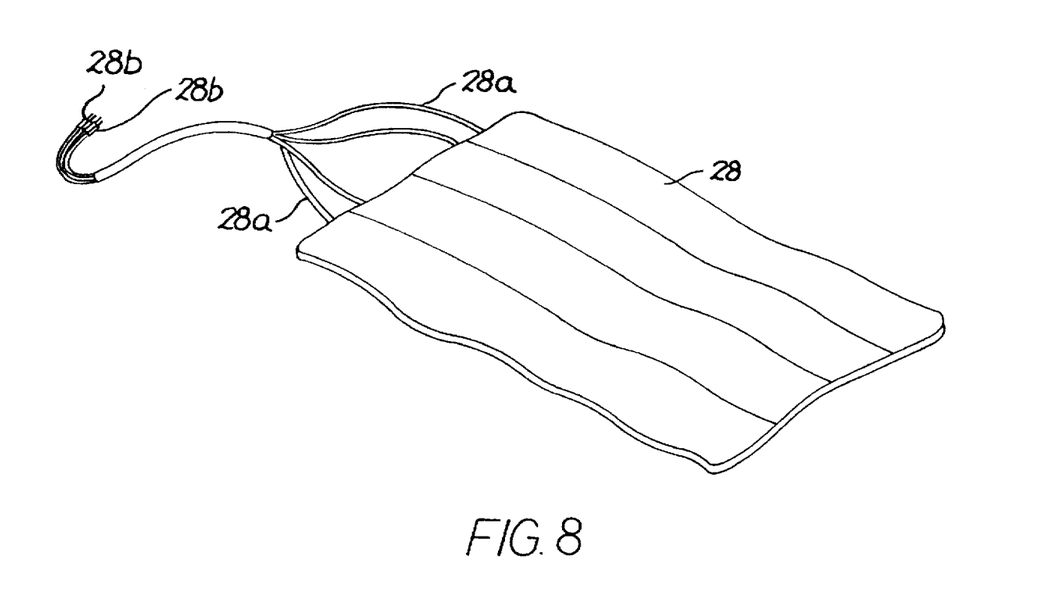
FIG. 8 shows a conventional perspective of a long cushion and its connectors.
Figure 9:
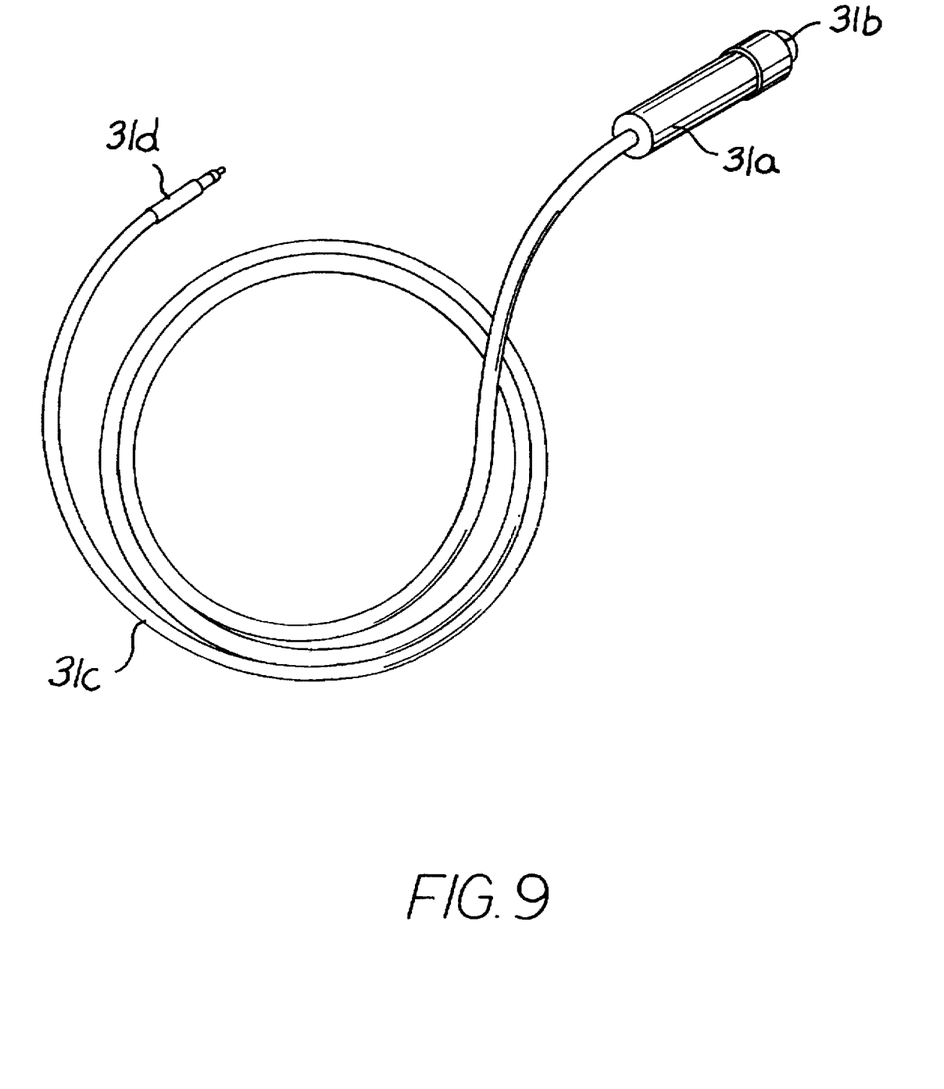
FIG. 9 shows a conventional perspective of a rotating pointer and its connecting cable.
Figure 10:
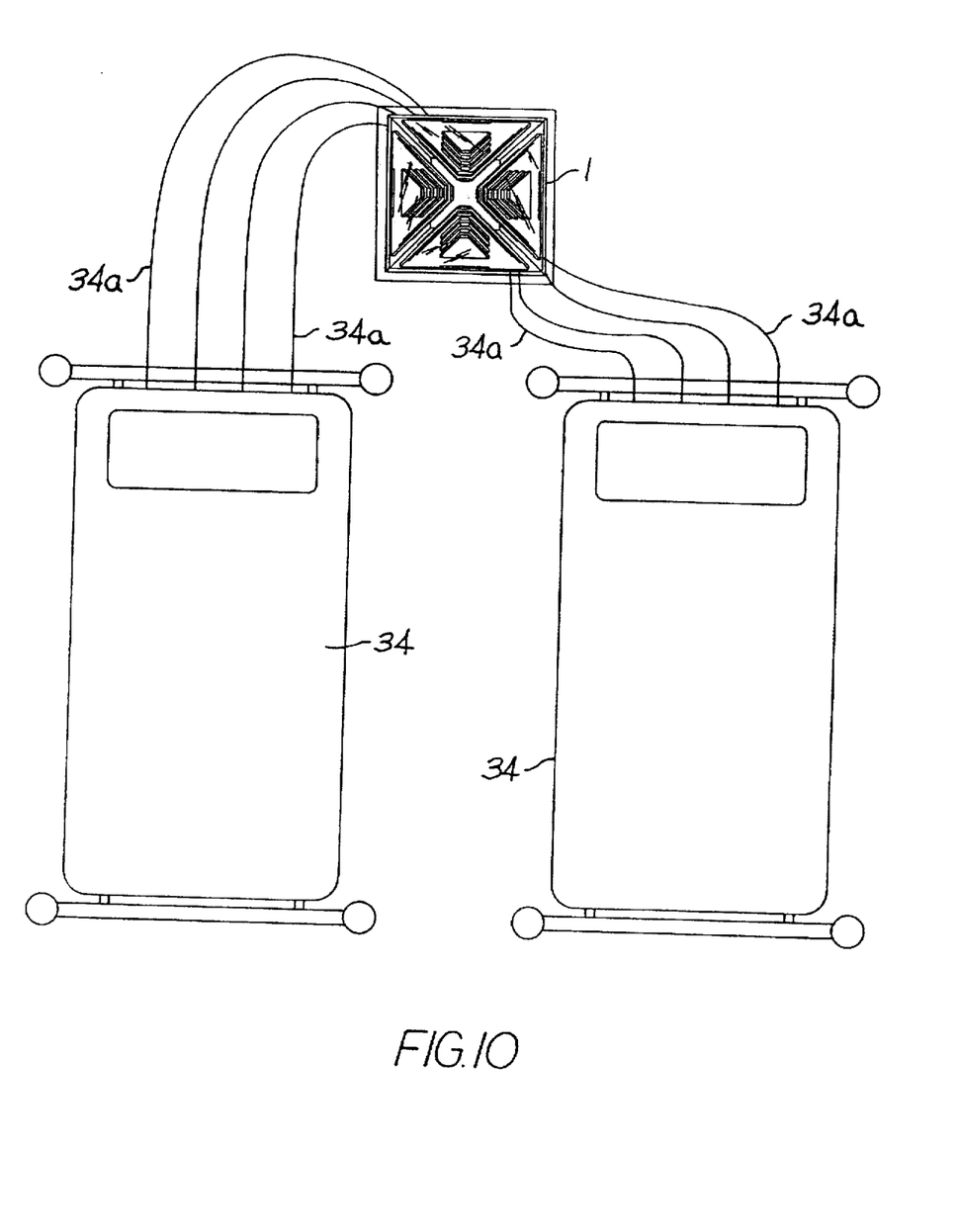
FIG. 10 shows a schematic view of how two beds or long cushions are interconnected to the reactor.
Figure 11:
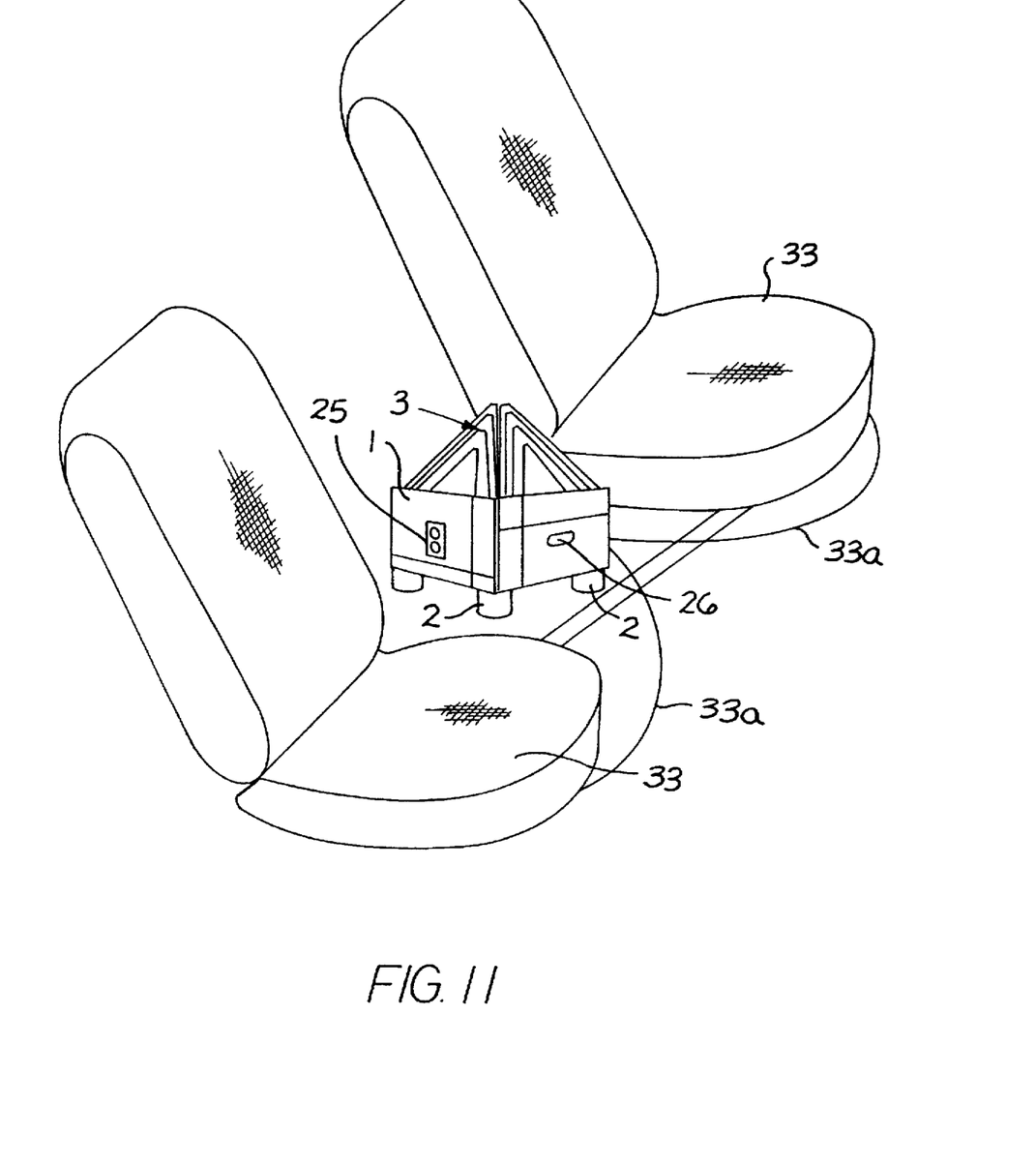
FIG. 11 shows a perspective of two car seats interconnected to a reactor.
Figure 12:
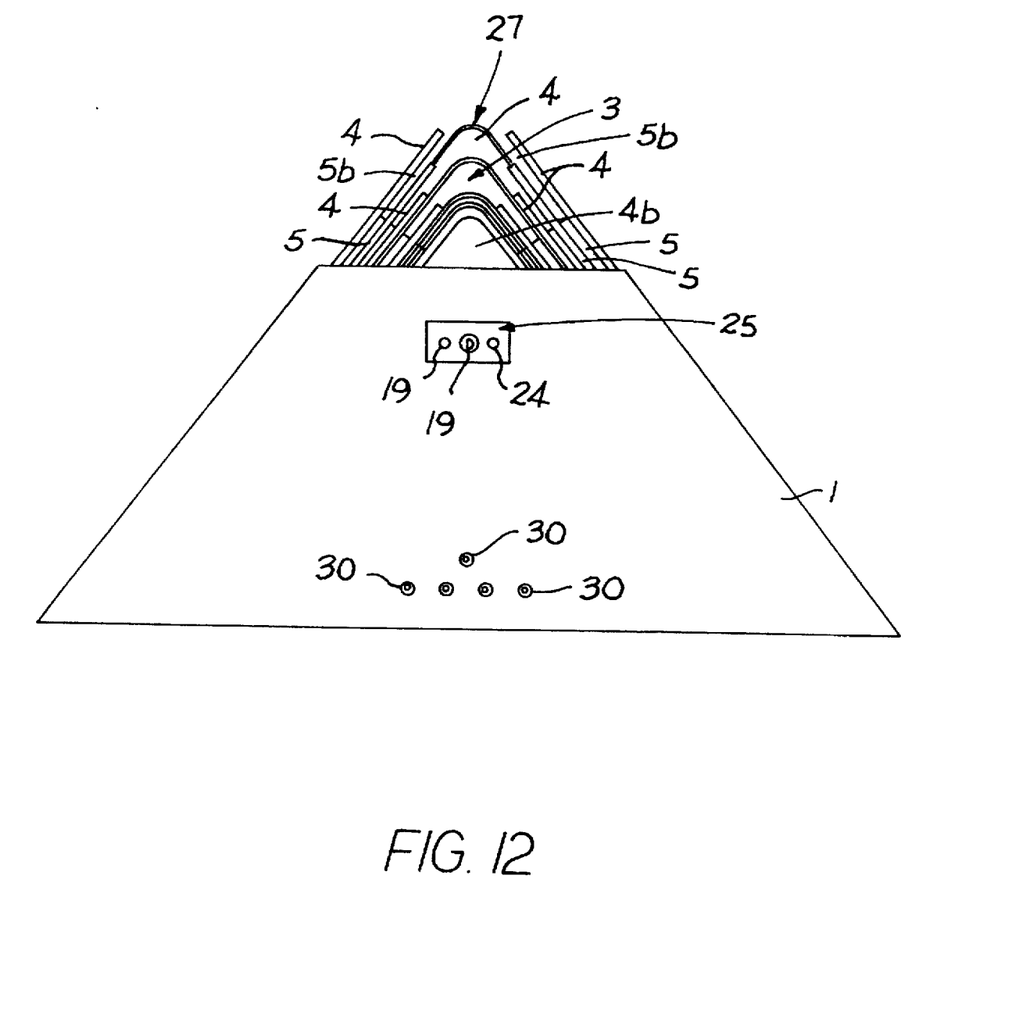
FIGS. 12 and 13 show some of the forms the reactor may adopt.
Figure 13:
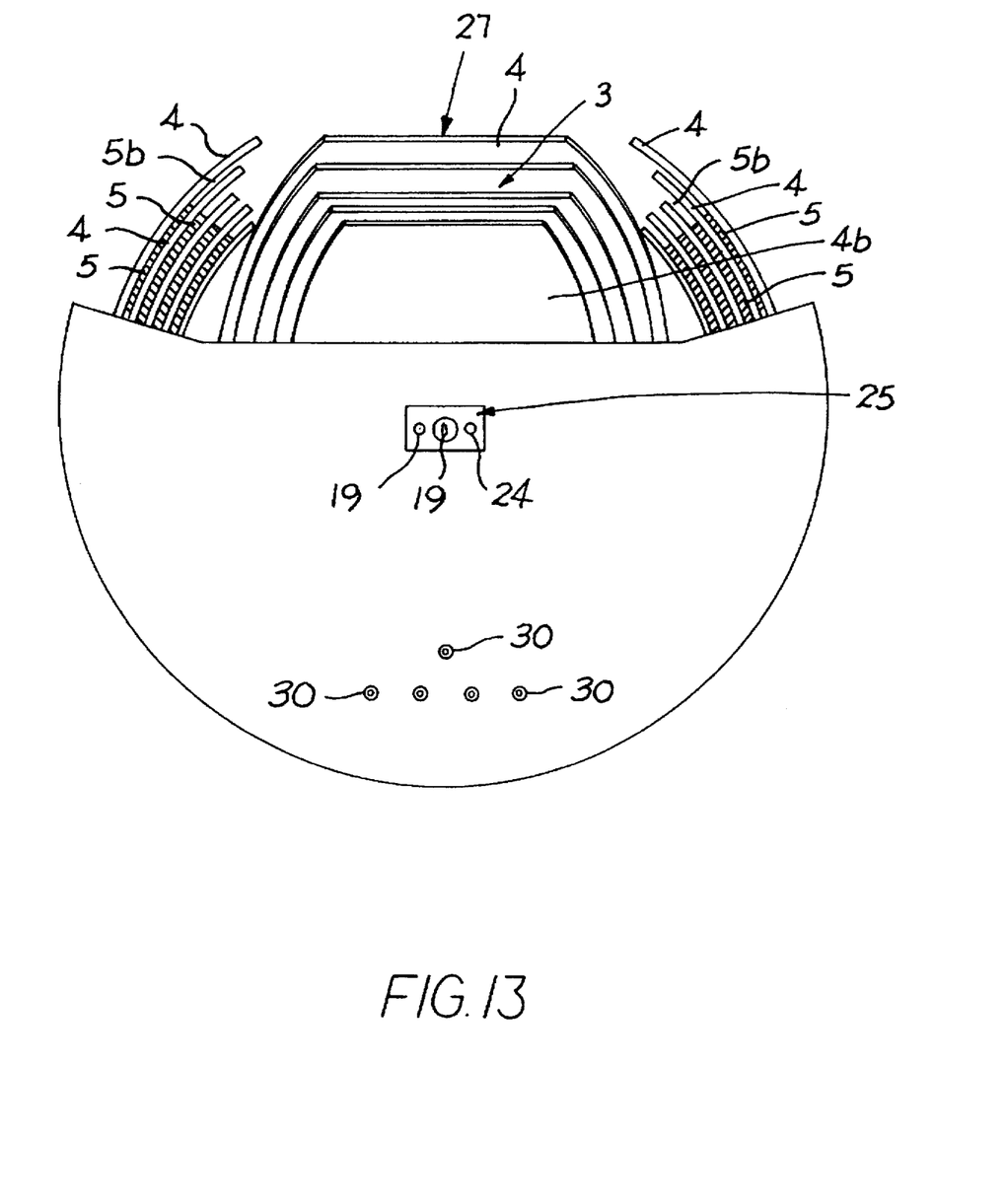
Figure 14:
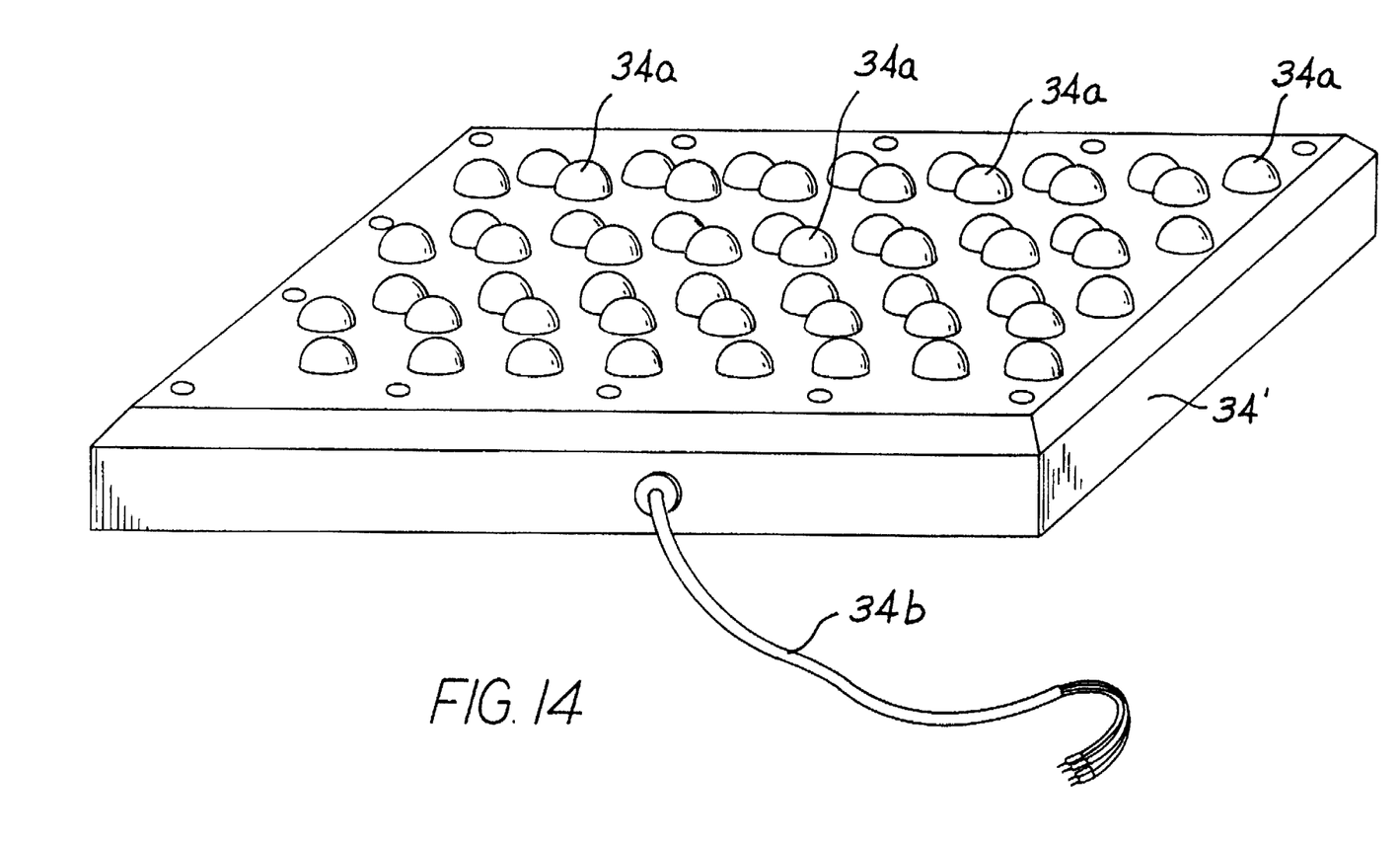
FIG. 14 shows a conventional view of a platform to stimulate preferably the feet.

As it has been clearly illustrated in FIGS. 7 and 11, the invention also includes as part of its elements, cushions (32) that can be placed over chairs or car seats, that by means of its cable (32A) and its connector (32B) may be connected to the sockets (30). It may also include beds (34) that by means of their cables (34A) can be connected to the apparatus (1).

Long cushions (28) as well as cushions (32) have an electricity contacting mesh (35) inside, which is interconnected to the cables (28A, 32A, 33A).

If the reactor is portable (FIG. 11) and it works with batteries, the invention may comprehend in combination, car seats (33) which by means of their cables (33A) and their connectors (33B) may be connected to the reactor's sockets (30).

Also for its easy operation, in two of the box's walls (1) there are some hollows (26) which facilitate the reactor's transportation from one place to another.

OPERATING METHOD

In order to operate the reactor and obtain the results for which it has been built, it must be placed in any open or closed place, connected to an electric source, and the circuit turned on, regulating the necessary intensity according with the size of the area that wants to be influenced with the operation of the reactor. This way, the air circulation will be obtained through the reactor's components and its plates, so when being in its atmosphere, one can breath and obtain the corresponding benefit; or else, either laying over the long cushion (28), or seated over the seats (32 and 33), or using the rotating pointer (31) or the sliding transmitter (36) over the skin surface, the organism molecules are reactivated with the electromagnetic energy coming from the reactor; it has been proved, by means of continuous physical and biological tests, that human cells increase their energetic resources to benefit the different organs that maintain the organism's vitality, because with the physical influence of the reactor they are stimulated cleaned and regenerated, because atoms are magnified without destruction.

What is claimed is:

1. A reactor system for creating electromagnetism fields and modifying the environment, comprising in combination:

a housing structure converging symmetrically at an upper end region outlet opening formed of a dielectric material to provide a container body within outer walls, said upper end region comprising glass plates interleaved with non-ferrous metallic plates in a symetrical array converging toward an upper apex beneath which is mirror reflecting the converging plate structure in symmetrically equal images, a power cord for supplying an electrical voltage, a transformer located in said container body beneath the mirror coupled to said electrical voltage and means for varying the transformer output voltage, an electrical fan located in a lower cabinet body position, switching means for activating the fan from the power cord to form air turbulence passing by the transformer and out the apex opening, external electrically operated accessories for massaging a user's body, connections and cables for deriving a high voltage from said transformer, socket means in said walls for connecting said external accessories to the electrical power cord, and means for positioning a person at rest in the vicinity of the container body.

2. The reactor system of claim 1, wherein said glass plates are longer than said metallic plates.

3. The reactor system of claim 1, providing air passage channels passing between portions of said interleaved plates.

4. The reactor system of claim 1, having an external electrical accessory connected to said socket means, comprising a cushion.

5. The reactor system of claim 4, wherein said cushion accessory has an internal electrically conducting mesh coupled electromagnetically to said reactor by a connector cable.

6. The reactor system of claim 1, having an external accessory connected to said socket means having an electrically actuated massaging head for body treatment of a user in the vicinity of the container body.

7. A reactor system for positioning users in the presence of electromagnetic energy and a turbulent air flow path, comprising in combination:

an enclosure of dielectric material presenting walls and an upper opening formed of alternating glass and metal plates forming a pyramid arrangement with an air flow path directed between said plates toward an exit apex;

a transformer located in said enclosure beneath the apex;

an electric fan located in said enclosure beneath the transformer for passing a turbulent flow of air toward said apex;

a set of sockets for connecting external electrically actuated accessories;

a pattern of electrical cables connecting an electrical power source to said fan, transformer and sockets;

an on-off electrically operated movable massaging accessory electrically coupled with one of the sockets, and a body positioning cushion for supporting a user person in a position to breath air emitted by said exit apex and to use said accessory.

\* \* \* \* \*